United States Patent
Seo et al.

(10) Patent No.: US 10,889,794 B2
(45) Date of Patent: Jan. 12, 2021

(54) APPARATUS FOR MEASURING CELL ACTIVITY AND METHOD FOR ANALYZING CELL ACTIVITY

(71) Applicant: KOREA UNIVERSITY RESEARCH AND BUSINESS FOUNDATION, SEJONG CAMPUS, Sejong-si (KR)

(72) Inventors: Sung-Kyu Seo, Yongin-si (KR); Geon-Soo Jin, Busan (KR); Un-Hwan Ha, Daejeon (KR); Se-Hwan Paek, Seoul (KR); Seung-Pil Pack, Daejeon (KR)

(73) Assignee: KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 451 days.

(21) Appl. No.: 14/385,829

(22) PCT Filed: Dec. 27, 2012

(86) PCT No.: PCT/KR2012/011555
§ 371 (c)(1),
(2) Date: Sep. 17, 2014

(87) PCT Pub. No.: WO2013/147398
PCT Pub. Date: Oct. 3, 2013

(65) Prior Publication Data
US 2015/0050684 A1  Feb. 19, 2015

(30) Foreign Application Priority Data

Mar. 30, 2012  (KR) .................. 10-2012-0032808
Dec. 3, 2012   (KR) .................. 10-2012-0138741

(51) Int. Cl.
*G01N 21/01*   (2006.01)
*G01N 33/487*  (2006.01)
(Continued)

(52) U.S. Cl.
CPC ........... *C12M 41/46* (2013.01); *G01J 1/0295* (2013.01)

(58) Field of Classification Search
CPC ..... C12M 41/46; G01N 21/01; G01N 33/487; G01N 33/48735; G01N 2021/0181; G01J 1/0295
See application file for complete search history.

(56) References Cited

U.S. PATENT DOCUMENTS 5,348,883 A * 9/1994 Togawa .................. B01L 3/508
                                                   422/939
2004/0241832 A1* 12/2004 Muraki .................. C12M 41/46
                                                   435/287.1
(Continued)

FOREIGN PATENT DOCUMENTS

KR  1020100098107 A  9/2010
KR  1020110018798 A  2/2011
(Continued)

OTHER PUBLICATIONS

Lange et al.,"Sensors and Actuators B-Chem, 107 (2005): p. 904-914".*
(Continued)

*Primary Examiner* — Liban M Hassan
(74) *Attorney, Agent, or Firm* — Hauptman Ham, LLP

(57) ABSTRACT

The present invention relates to an apparatus that uses shadow images of cells to continuously measure cell activity at a high processing rate in order to provide cell activity and cell number results. According to one embodiment of the present invention, instead of a highly experienced examiner or technician using a microscope, ELISA reader, etc. having to collect various cell activity measurements and cell numbers, the collection of said information can be automated so as to reduce cost and largely reduce errors in measurements through the development of computer software coupled with (Continued)

hardware using low cost and compact optoelectronic components and simple image processing techniques.

3 Claims, 16 Drawing Sheets

(51) Int. Cl.
  *G01J 1/02* (2006.01)
  *C12M 1/34* (2006.01)

(56) References Cited

U.S. PATENT DOCUMENTS

| | | | |
|---|---|---|---|
| 2006/0119836 A1* | 6/2006 | Ku | G01N 15/147 356/39 |
| 2009/0179159 A1* | 7/2009 | Yamada | G01N 21/474 250/459.1 |
| 2010/0231909 A1* | 9/2010 | Trainer | G01B 11/08 356/336 |
| 2010/0246927 A1 | 9/2010 | Arbuckle | |

FOREIGN PATENT DOCUMENTS

| | | | |
|---|---|---|---|
| KR | 10-1038484 B | 6/2011 | |
| KR | 1020110129078 A | 12/2011 | |
| WO | WO 2008090330 A1 * | 7/2008 | ......... G01N 15/1456 |
| WO | 2011/049965 A1 | 4/2011 | |

OTHER PUBLICATIONS

Su et al. (High-Through Lensfree Imaging and Characterization of a Heterogeneous Cell Solution on a Chip, 102 (3):856-868 (Year: 2009).*

Moon et al.,"Enumeration of CD4+ T-Cells using a portable microchip count platform in Tanzanian HIV-infected patients". (Year: 2011).*

Multi-color LUCAS: Lensfree On-chip Cytometry Using Tunable Monochromatic Illumination and Digital Noise Reduction, 2008; pp. 146-156 (Year: 2008).*

Sungkyu Seo et al., "High-Throughput Lens-Free Blood Analysis on a Chip", Anal Chem., Jun. 25, 2010, pp. 4621-4627, vol. 82, No. 11.

Aydogan Oacan et al., "Ultra wide-field lens-free monitoring of cells on-chip", Lab on a Chip, 2008, pp. 98-106, vol. 8, The Royal Society of Chemistry.

International Search Report for application No. PCT/KR2012/011555 dated Apr. 22, 2013.

Office Action dated Sep. 27, 2013 from Korean Patent Office in connection with the counterpart Korean patent application No. 10-2012-0138741.

Notice of Allowance dated Jan. 22, 2014 from Korean Patent Office in connection with the counterpart Korean patent application No. 10-2012-0138741.

* cited by examiner

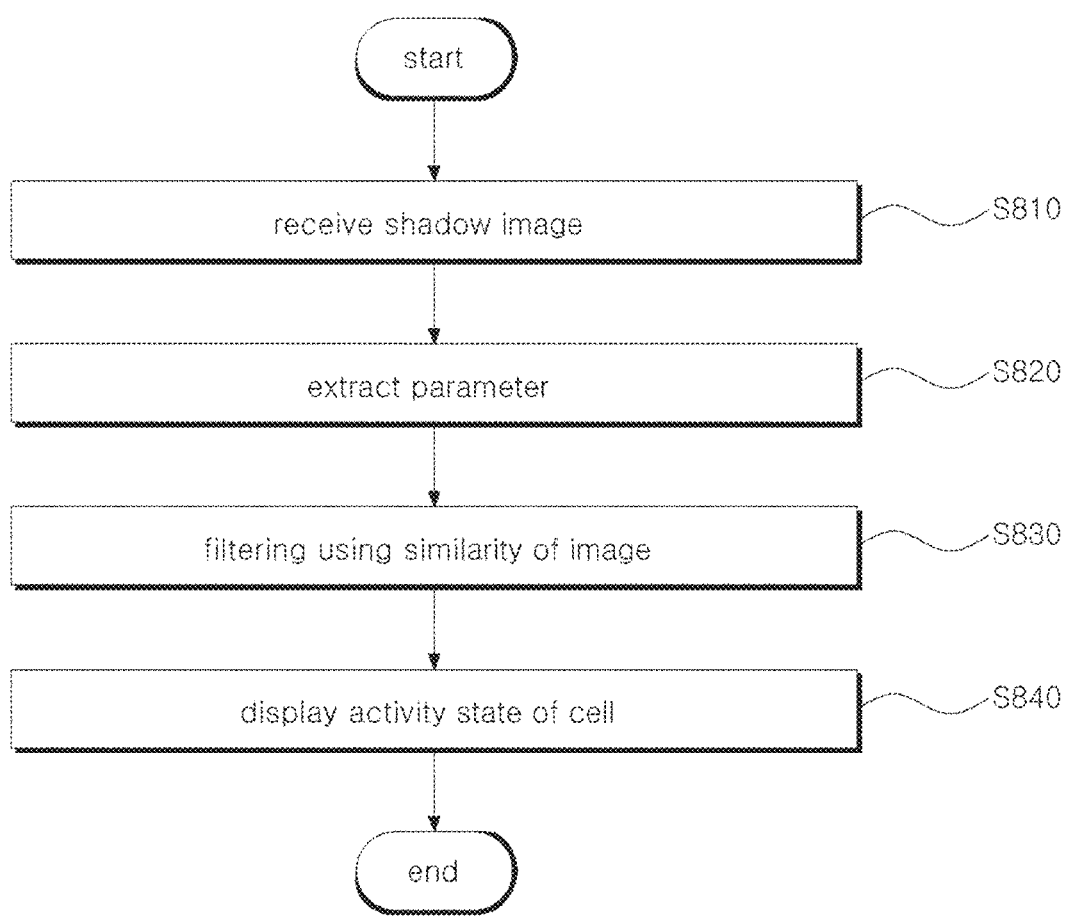

APPARATUS FOR MEASURING CELL ACTIVITY AND METHOD FOR ANALYZING CELL ACTIVITY

CROSS-REFERENCE TO RELATED APPLICATIONS

This application is a National Phase Application of PCT International Application No. PCT/KR2012/011555, which was filed on Dec. 27, 2012, and which claims priority from Korean Patent Application No. 10-2012-0032808, filed with the Korean Intellectual Property Office on Mar. 30, 2012, and Korean Patent Application No. 10-2012-0138741, filed with the Korean Intellectual Property Office on Dec. 3, 2012. The disclosures of the above patent applications are incorporated herein by reference in their entirety.

BACKGROUND

1. Technical Field

The present invention relates to an apparatus for measuring cell activity and a method for analyzing cell activity, more particularly to a cell activity measurement apparatus that uses shadow images of cells to measure cell activity continuously and at a high processing rate and a cell activity analysis method that can analyze the measured cell activity.

2. Description of the Related Art

Observing the activity of cells or whether the cells are living or dead is an important step in developing modern medicines or foods. The reactivity of cells to a particular drug or specimen or observing whether the cells are living or dead is essential to the research process. Some of the traditional techniques developed for observing the proliferation or activity of cells are as follows.

ELISA (enzyme-linked immunosorbent assay), which uses an antibody having good specificity and high sensitivity together with an enzyme serving as a signal source, is a technique that selectively reacts cells that are in a particular state and measures the absorbency.

Western blots refer to a method of detecting proteins by electrophoresis. First, the proteins are separated by polyacrylamide gel electrophoresis, and then the positions of the electrophoresis separations are moved directly to a membrane, so as to detect certain proteins by radioimmunoassay.

Immunohistochemistry is a method that uses a labeled antibody to visualize certain antigens present in a tissue or a cell, so that they may be observed through an optical microscope or an electron microscope.

The methods listed above require large, expensive equipment or entail dyeing cells and observing through a microscope or measuring absorbency, etc., for the measuring of cell activity and determining whether the cells are living or dead, and hence require high costs, a complicated system, and a large space. Also, since the specimen must inevitably be destroyed for analysis, it is impossible to observe certain cells continuously.

Therefore, research is needed for a technology for measuring cell activity that allows for quick and widespread use, without requiring a separate reagent, and without destroying a specimen.

SUMMARY

An objective of the present invention is to provide a cell activity measurement apparatus based on shadow imaging technology with which cells can be observed continuously without destroying the specimen and without requiring a separate reagent treatment.

An objective of the present invention is to provide a cell activity analysis method that analyzes the activity of cells by extracting certain parameters from a shadow image of the cells captured via an image sensor.

To achieve the objectives above, an embodiment of the present invention provides a cell activity measurement apparatus that includes: a fluidic channel in which a culture fluid and a cell are injected; a light-emitting element positioned over the fluidic channel to emit light in a direction of the fluidic channel; and an image sensor positioned under the fluidic channel to capture a shadow image of the cell.

To achieve the objectives above, an embodiment of the present invention provides a cell activity measurement apparatus that includes: a well plate in which a culture fluid and a cell are injected; a light-emitting element positioned over the well plate to emit light in a direction of the well plate; and an image sensor positioned under the well plate to capture a shadow image of the cell.

To achieve the objectives above, an embodiment of the present invention provides a cell activity measurement apparatus that includes: a cell chip, which provides a cell storage place for injecting a culture fluid and a cell, and which has a small thickness of 0.1 mm-1.0 mm for its bottom surface; a light-emitting element positioned over the cell chip to emit light in a direction of the cell chip; and an image sensor positioned under the cell chip to capture a shadow image of the cell.

To achieve the objectives above, an embodiment of the present invention provides a cell activity measurement apparatus that includes: a light-emitting element configured to emit light; and an image sensor positioned under the light-emitting element to receive a cell storage means placed thereon, where the cell storage means includes a space in which a cell and a culture fluid are injected, and the image sensor is configured to capture a shadow image of the cell.

To achieve the objectives above, an embodiment of the present invention provides a cell activity analysis method that includes: receiving a shadow image captured by an image sensor; calculating a particular parameter from the received shadow image; and displaying an activity state of a cell by using the calculated parameter.

A cell activity measurement apparatus according to an embodiment of the present invention uses a simple, inexpensive setup while allowing a continuous observation of a large amount of cells without employing a separate reagent.

According to an embodiment of the invention, work that could only be performed by experienced examiners or technicians who are capable of using various cell activity measurement equipment such as a microscope, etc., can be automated with the development of computer software coupled with a simple image processing technique, with the results of decreased costs and greatly reduced errors in measurement.

Also, a cell activity analysis method according to an embodiment of the invention may use pixel values from the shadow image of cells, so that the activity of the cells can be easily analyzed without expensive microscopes or devices such as ELISA Reader.

Additional aspects and advantages of the present invention will be set forth in part in the description which follows, and in part will be obvious from the description, or may be learned by practice of the invention.

BRIEF DESCRIPTION OF THE DRAWINGS

FIG. 8 is a flow diagram illustrating a cell activity analysis method related to an embodiment of the present invention.

Figure 1:
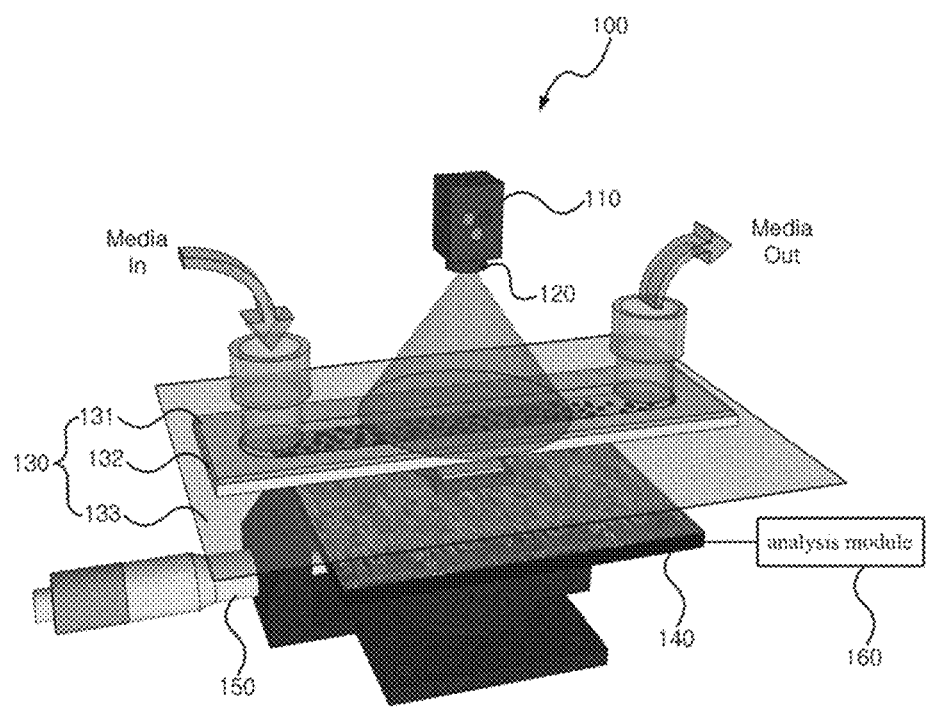
FIG. 1 shows a cell activity measurement apparatus related to an embodiment of the present invention.

DESCRIPTION OF NUMERALS 100, 300, 400, 500: cell activity measurement apparatus
110: light-emitting element
120: pinhole
130: fluidic channel
131: flow cell
132: wall
133: cover glass
140: image sensor
150: distance adjustment part
160: analysis module
170: temperature adjustment part

DETAILED DESCRIPTION

An apparatus for measuring cell activity and a method for analyzing cell activity related to an embodiment of the present invention will be described below in more detail with reference to the accompanying drawings. The cell activity measurement apparatus according to an embodiment of the invention can be implemented in various ways according to the form of the cell storage means. The cell storage means refers to a means that includes a space in which cells are injected and cultivated or measured. For example, the cell storage means can include a fluidic channel, a well plate, a cell chip, etc.

In the present specification, an expression used in the singular encompasses the expression of the plural, unless it has a clearly different meaning in the context. In the present specification, terms such as "comprising" or "including," etc., should not be interpreted as meaning that all of the components or operations are necessarily included. That is, some of the components or operations may not be included, while other additional components or operations may be further included.

FIG. 1 shows a cell activity measurement apparatus related to an embodiment of the present invention. The cell activity measurement apparatus 100 here uses a fluidic channel as the cell storage means.

As illustrated in the drawing, the cell activity measurement apparatus 100 can include a light-emitting element 110, a pinhole 120, a fluidic channel 130, an image sensor 140, a distance adjustment part 150, and an analysis module 160.

The light-emitting element 110 may emit light by which to capture the shadow image of the cells. The light-emitting element can be positioned at the fluidic channel 130 into which the cells and a culture fluid (medium or media) may be injected. The light-emitting element 110 can include an RGB light-emitting diode (LED) for a clear capture of the shadow image.

The pinhole 120 can be coupled to a lower end of the light-emitting element 110 to clarify the shadow image of the cells. That is, the pinhole 120 can be used for increasing the coherence and illuminance of the light.

The pinhole 120 can be fabricated in the form of a film mask made of a plastic material. The film mask pinhole of a plastic material can be printed on an OHP film, etc., with a high-resolution laser printer and attached in front of the light-emitting element 110, so that it is much more inexpensive to fabricate compared with a pinhole of a metallic material and can be fabricated easily. Also, in the case of a multi-wavelength light source such as an RGB light-emitting diode where individual light sources for three colors (red, green, and blue) are integrated in one light-emitting diode, three pinholes may be positioned with a gap of several tens of micrometers in-between, but by using a method of printing with a high-resolution laser printer, the multiple pinholes can be easily designed on a computer.

Inside the fluidic channel 130, a space may be prepared into which the cells and the culture fluid may be injected and in which the cells can be cultivated. The fluidic channel can be formed such that the channel has a width of several mm or smaller, and thus can reduce the volume of the culture fluid including the cells that is injected therein. A reason for this is because a high concentration of cells used for the activity measurement can result in great noise during the analysis of the shadow image.

Also, at least a portion of the sidewall of the fluidic channel 130 can be implemented with a polydimethylsiloxane (PDMS) material. A reason for this implementation is that a supply of oxygen may be required for the cultivation of cells, and the inherent properties of the polydimethylsiloxane (PDMS) material allow a permeation of oxygen. Thus, in cases where at least a portion of the sidewall is implemented with a polydimethylsiloxane (PDMS) material, a separate oxygen supply device may not be required.

The fluidic channel 130 can include a flow cell 131, a wall 132, and a cover glass 133.

The flow cell 131 may be where the cells and the culture fluid are injected and discharged and can serve as a cover for the fluidic channel 130. The flow cell 131 can be fabricated using a material such as glass, plastic, quartz, etc.

The wall 132 can be made of a polydimethylsiloxane (PDMS) material and can be fabricated with a hollow middle portion so as to provide a space between the flow cell 131 above and the cover glass 133 below in which the cells may grow without permitting the culture fluid to leak. In cases where the wall 132 is implemented with a PDMS material, the properties of the PDMS material can enable the permeation of oxygen, which is essentially required for cell cultivation. Thus, it may not be necessary to provide the fluidic channel 130 with a separate oxygen supply device. The wall 132 can be fabricated with a thickness of about 1 mm, to allow a smaller size for the cell activity measurement apparatus 100.

The cover glass 133 can be positioned at the lower end of the wall 132 and can serve as the bottom of the fluidic channel 130.

The image sensor 140 can capture the shadow image of the cells at the lower portion of the fluidic channel 130. The image sensor 140 can be implemented as a CMOS (complementary metal-oxide semiconductor) image sensor. The CMOS image sensor is an image-capturing element that has low power consumption and has a complementary metal-oxide semiconductor (CMOS) structure. The image sensor 140 can be implemented in a form that has no lens. The CMOS image sensor has a fast processing speed and has a low cost because it can be provided by mass production using semiconductor processes. Also, it has a broader observing range compared to an image sensor-based microscope using lenses and enables quantification and automation of the analysis.

The distance adjustment part 150 can be coupled with the image sensor 140 to adjust the distance between the image sensor 140 and the fluidic channel 130. That is, the distance adjustment part 150 can serve to finely adjust the position of the image sensor 140 to decrease the distance between the cover glass 133 and the image sensor 140 as much as possible and capture the shadow image with high contrast.

The analysis module 160 may serve to analyze the shadow image captured with the image sensor 140 by way of an image processing technique. The functions of the analysis module 160 will be described later in more detail.

Also, the cell activity measurement apparatus 100 can further include a temperature adjustment part for keeping the cultivated cells at a constant temperature.

Figure 2:
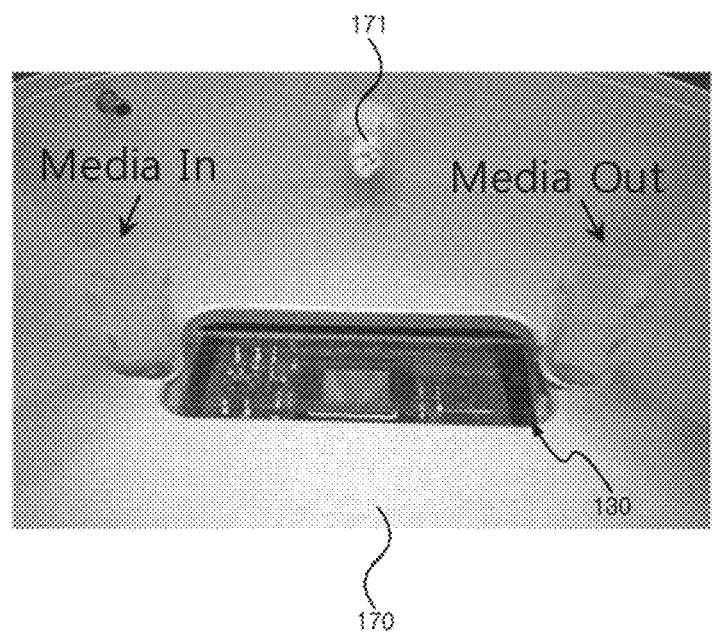
FIG. 2 illustrates the fluidic channel of FIG. 1 surrounded by a temperature adjustment part.

FIG. 2 illustrates the fluidic channel of FIG. 1 surrounded by a temperature adjustment part.

As illustrated in the drawing, the temperature adjustment part 170 can surround the fluidic channel 130 to serve as an incubator such that the cells may be cultivated at a constant temperature (e.g. 37° C.). The temperature adjustment part 170 may be capable of temperature control and can include a temperature sensor 171.

The shadow image of the cells captured by way of the image sensor 140 can be transferred to the analysis module 160 where the activity state of the cells may be analyzed.

Figure 3:
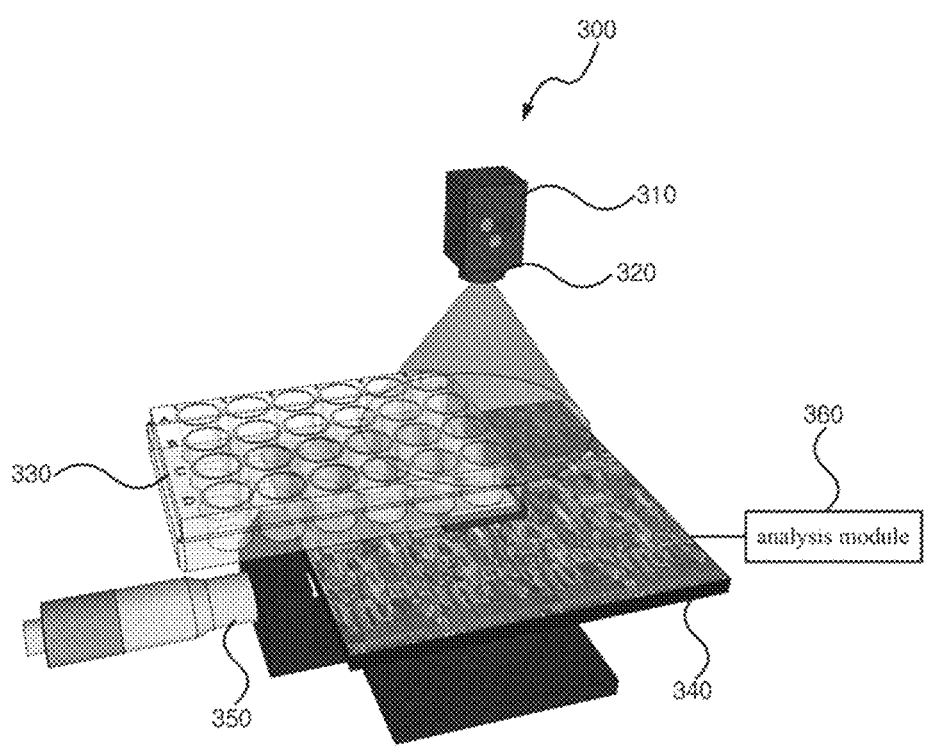
FIG. 3 to FIG. 5 show a cell activity measurement apparatus related to another embodiment of the present invention.

FIG. 3 shows a cell activity measurement apparatus related to an embodiment of the present invention. The cell activity measurement apparatus 300 here uses a well plate as the cell storage means.

As illustrated in the drawing, the cell activity measurement apparatus 300 can include a light-emitting element 310, a pinhole 320, a well plate 330, an image sensor 340, a distance adjustment part 350, and an analysis module 360.

The components illustrated in FIG. 1 can be applied in like manner for the light-emitting element 310, pinhole 320, image sensor 340, distance adjustment part 350, and analysis module 360, and as such, the detailed descriptions of these components are omitted here.

The well plate 330 may be positioned under the light-emitting element 310 and may have a multiple number of wells formed therein. A well refers to a space into which a specimen can be injected.

For example, a 96-well plate or a 24-well plate can be used for the well plate 330. A 96- or a 24-well plate refers to a well plate in which 96 or 24 wells are formed.

In order to obtain a shadow image in which optical losses are minimized, the well plate 330 can be a black well plate, which has a thin well bottom and has little optical interference.

Also, the well plate 330 can be fabricated to be capable of movement, to allow changes in the point at which the radiation from the light-emitting element 310 arrives or changes in the point at which the sensing by the CMOS image sensor 340 occurs. For example, the well plate 330 can be fabricated to be rotatable.

Also, the cell activity measurement apparatus 300 can further include a temperature adjustment part for keeping the cultivated cells at a constant temperature.

Figure 4:
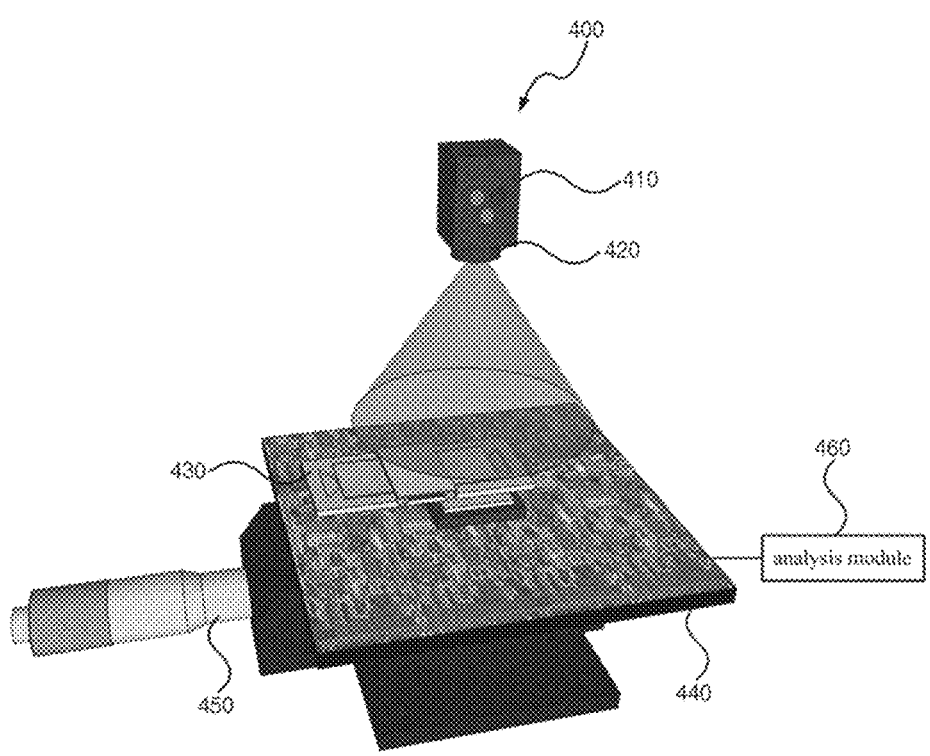

FIG. 4 shows a cell activity measurement apparatus related to an embodiment of the present invention. The cell activity measurement apparatus 400 here uses a cell chip as the cell storage means.

As illustrated in the drawing, the cell activity measurement apparatus 400 can include a light-emitting element 410, a pinhole 420, a cell chip 430, an image sensor 440, a distance adjustment part 450, and an analysis module 460.

The components illustrated in FIG. 1 can be applied in like manner for the light-emitting element 410, pinhole 420, image sensor 440, distance adjustment part 450, and analysis module 460, and as such, the detailed descriptions of these components are omitted here.

The cell chip 430 may be a cell storage means that is implemented in the form of a chip that is provided with a space in which to inject the cells and the culture fluid. The cell chip 430 may be a biochip that can detect the activity of cells or complex physiological signals caused by cells and can be used for the purposes of counting the cells.

A typical cell chip may be used with two optically transparent sheets of glass, plastic, or polymer material, as an upper substrate and a lower substrate, attached or assembled together with a space in-between for storing the cells, and in the case of a cell chip 430 for cell shadow imaging as used in an embodiment of the present invention, a small thickness of about 0.1 mm-1.0 mm may be used for the thickness of the lower substrate. Also, in the case of a cell chip that is fabricated in an integrated form without attaching or assembling with a space in-between for storing the cells, the thickness of the lower substrate may be small, being about 0.1 mm-1.0 mm.

Figure 5:
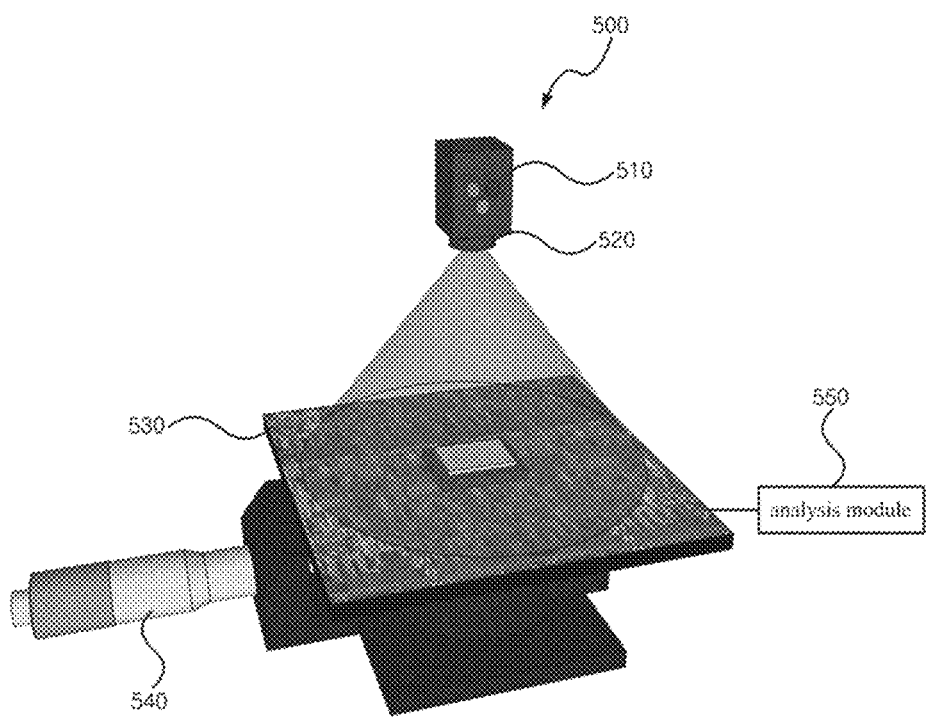

FIG. 5 shows a cell activity measurement apparatus related to an embodiment of the present invention.

As illustrated in the drawing, cell activity measurement apparatus 500 can include a light-emitting element 510, a pinhole 520, an image sensor 530, a distance adjustment part 540, and an analysis module 550.

The components illustrated in FIG. 1 can be applied in like manner for the light-emitting element 510, pinhole 520, image sensor 530, distance adjustment part 540, and analysis module 550, and as such, the detailed descriptions of these components are omitted here.

However, the image sensor 530 can be implemented such that a cell storage means can be placed thereon in a stable manner.

The cell activity measurement apparatus 500 does not include the cell storage means as a component, but rather provides a space in which to receive the cell storage means. That is, the cell activity measurement apparatus 500 may be prepared with a space where a cell storage means may be placed or received, and thus be implemented to allow replacements of the cell storage means in various forms as necessary, instead of being formed together with the cell storage means as a set. For example, the cell activity measurement apparatus 500 can have a well plate placed over the image sensor 530 to measure the activity of the cells when a well plate is required as the cell storage means, and can have a cell chip placed over the image sensor 530 to measure the activity of the cells when a cell chip is required as the cell storage means.

Also, the cell activity measurement apparatus 500 can use a particular cell storage means exclusively for placement or reception. For example, the cell activity measurement apparatus 500 can be fabricated such that a cell chip is placed thereon exclusively.

The cell activity measurement apparatuses 100, 300, 400, 500 described above can include the same analysis module.

Figure 6:
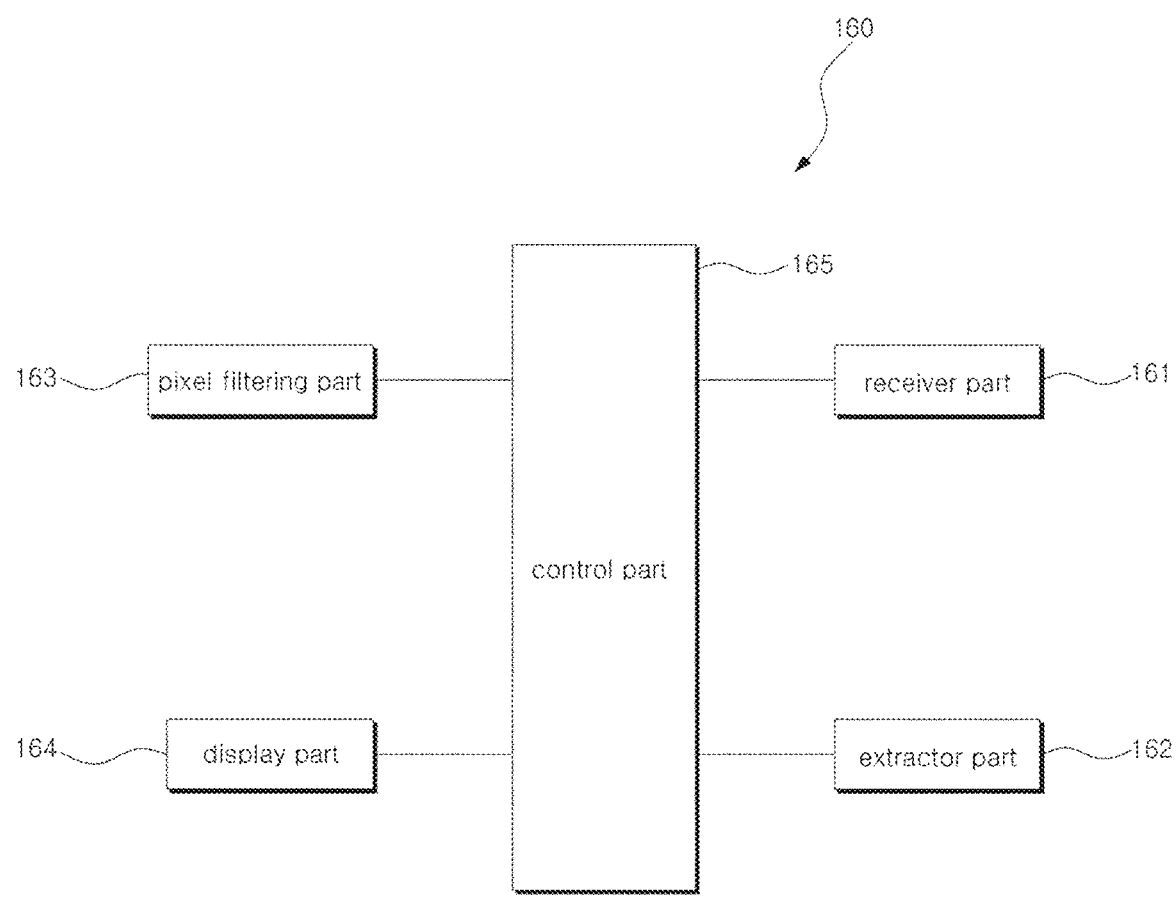
FIG. 6 is a block diagram of an analysis module related to an embodiment of the present invention.

FIG. 6 is a block diagram of the analysis module illustrated in FIG. 1.

The illustrated analysis module 160 can be implemented as a component of the cell activity measurement apparatus 100 but can also be implemented as a device that is separate from the cell activity measurement apparatus 100.

The analysis module 160 can include a receiver part 161, an extractor part 162, a pixel filtering part 163, a display part 164, and a control part 165.

The receiver part 161 can receive the shadow image from the image sensor 140. In cases where the analysis module 160 exists separately from the cell activity measurement apparatus 100, the receiving of the shadow image can be performed by various communication methods (e.g. wireless communication).

The extractor part 162 can calculate a particular parameter for analyzing cell activity from the shadow image. For example, an SNR (signal-to-noise ratio) value, an SD (shadow diameter) value, the maximum pixel value, the position of a pixel having the maximum value, the minimum pixel value, the position of a pixel having the minimum value, the diameter of the first bright ring, the diameter of the first dark ring, the width between a bright ring and a dark ring, the area of the shadow image, the circularity of the shadow image, and so on, can be a parameter for cell activity analysis.

The SNR (signal-to-noise ratio) refers to a log value taken after dividing the difference between the maximum intensity value from pixels specified to include cells and the average intensity value of the background that does not include cells by the standard deviation value of the background.

The SNR can be expressed as Equation 1.

$$SNR = 20 \log|(\max(I) - \mu_b)/\sigma_b|(dB)$$ [Equation 1]

Here, $\mu_b$ and $\sigma_b$ refer to the average background value of the shadow image and the standard deviation, respectively. The value max(I) is the maximum intensity pixel value.

Also, the SD (shadow diameter) is a value expressing the diameter of the cells' shadow image extracted from the intensity values of pixels specified to include the cells as a root mean square. The SD can be expressed as Equation 2.

$$SD = 2\sqrt{\sum_{x=1}^{n}(x-\bar{x})^2|f(x)|^2/\sum_{x=1}^{n}|f(x)|^2} \text{ (pixel)}$$ [Equation 2]

Here, n, x, and f(x) refer to the maximum number of pixels in the cell shadow area, the specified pixels, and the intensity values of the specified pixels, respectively.

The shadow image of the cells can be a circular image in which bright rings and dark rings appear in an alternating manner. In this case, the first bright ring from the center may be referred to as a first bright ring, and the first dark ring from the center may be referred to as a first dark ring.

Also, the circularity of a shadow image can be the measure of how similar the shadow image is to a circle.

The pixel filtering part 163 can specify certain pixels from the shadow image by using the particular parameter, similarity to a particular shape, etc. This will be described later in more detail.

The display part 164 can display the activity state of the cells by using items extracted at the extractor part 162 for cell activity analysis.

The control part 165 may control the overall functions performed at the receiver part 161, extractor part 162, pixel filtering part 163, and display part 164.

A method of analyzing the activity of cells is described below with reference to test examples.

In the present test example, human aveolar epithelial cells (A549) were used, which are epithelial cells of a human lung. The initial concentration was 250,000 cells/ml. The oxygen demand of the cells cultivated in the fluidic channel 130 was $5.795 \times 10^{-7}$ mol/day, but the amount of oxygen permeation at the wall 132 fabricated from a PDMS material was $1.771 \times 10^{-6}$ mol/day, so that no separate oxygen supply was necessary. A $CO_2$ independent medium (18045, GIBCO), which does not require a separate supply of $CO_2$, was used for the culture fluid that is injected for cell cultivation. The culture fluid was injected into the fluidic channel 130 at a rate of 5-10 μl/min by using a separate syringe pump (M200, KD Scientific). In the present test example, an RGB light-emitting diode was used for the light-emitting element 110, and a CMOS image sensor was used for the image sensor 140.

Figure 7A:
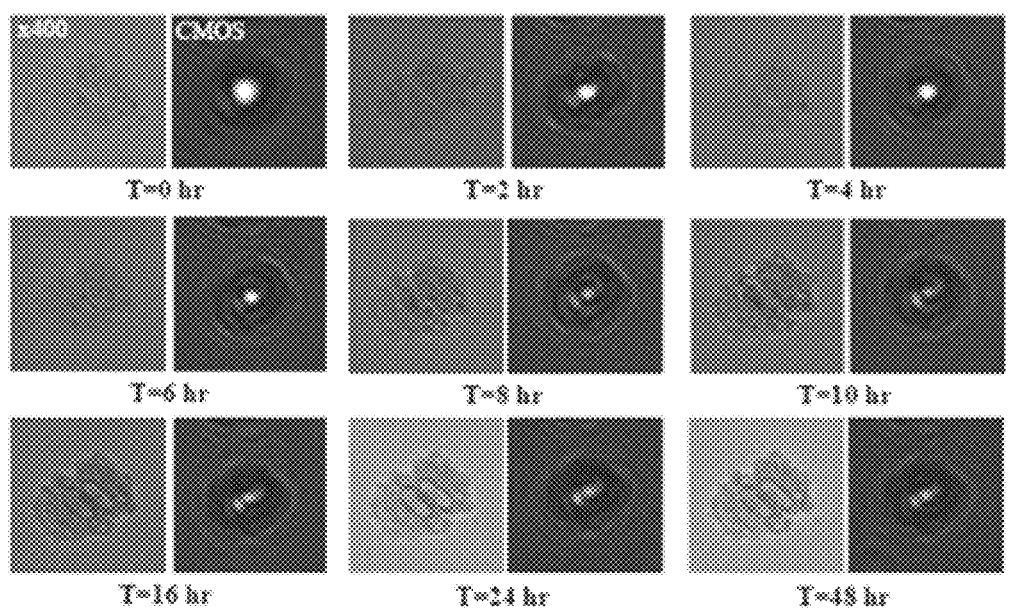
FIG. 7A, FIG. 7B, and FIG. 7c show a shadow image of cells captured by way of the cell activity measurement apparatus of FIG. 1 and an image of the cells captured by way of a microscope.
Figure 7B:
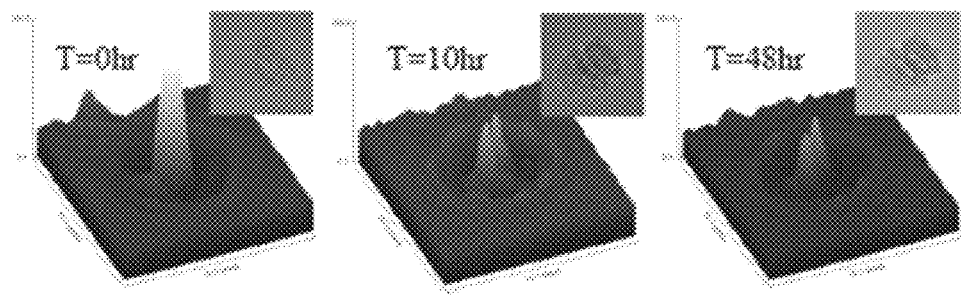
Figure 7C:
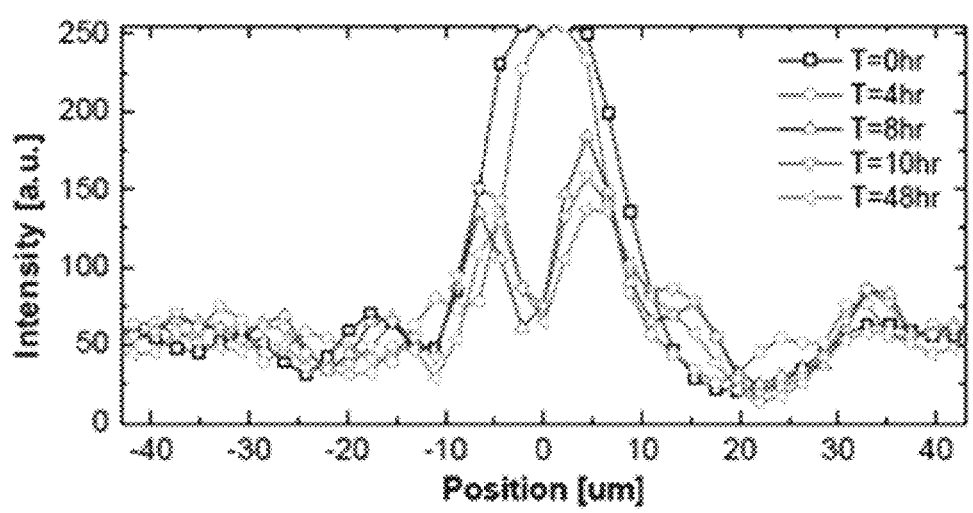

FIGS. 7A to 7C shows a shadow image of cells captured by way of the cell activity measurement apparatus of FIG. 1 and an image of the cells captured by way of a microscope.

By using the cell activity measurement apparatus 100, the nucleus division of a cell can be easily observed even without a microscope. The cell of interest was observed through the cell activity measurement apparatus 100 and a regular optical microscope concurrently for 48 hours, and the comparison results show that the nucleus division of the cell observed by the microscope (photographs on the left) is also observable in the cell's shadow image, as presented in FIG. 7A. By applying image processing techniques on these changes in the shadow image, the pixel values may be expressed as 3-dimensional (FIG. 7B) and 2-dimensional (FIG. 7C) graphs, from which it can be seen that rapid changes in the shadow pattern occurred between 4 hours and 10 hours, when the nucleus division occurred.

FIG. 8 is a flow diagram illustrating a cell activity analysis method related to an embodiment of the present invention.

The receiver part 161 can receive a shadow image of a cell captured by way of the image sensor 140 (S810).

The extractor part 162 can calculate a particular parameter from the cells' shadow image received (S820). In the test example, the SNR value and the SD value were extracted from among the parameters.

Then, the pixel filtering part 163 can specify particular pixels from the shadow image by using a degree of similarity to a particular shape (S830).

For example, the pixel filtering part 163 can choose and specify only the pixels of which the circularity corresponds to a particular range from among the pixels forming the shadow pattern of the cell.

The display part 164 can draft and display time-lapse graphs of the extracted SNR values and SD values (S840).

Figure 9A:
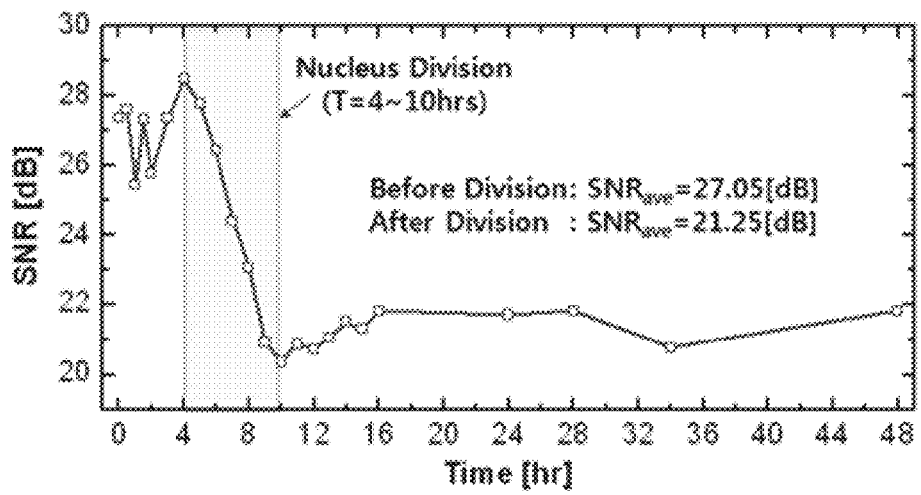
FIG. 9A and FIG. 9B illustrate a nucleus division state of a cell as captured by way of the cell activity measurement apparatus of FIG. 1.
Figure 9B:
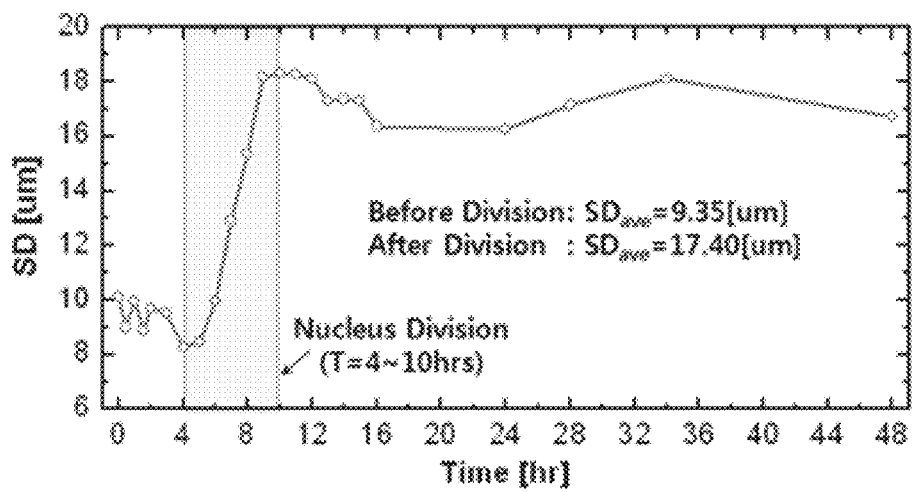

FIG. 9A and FIG. 9B show time-lapse graphs of the SNR values and SD values extracted from the shadow image of a cell used in the test example above.

As illustrated, the results of tracking the two items (SNR and SD) for 48 hours are shown in FIG. 9A and FIG. 9B.

FIG. 9A represents changes in the SNR, and FIG. 9B represents changes in the SD, and in both results, there are steep changes between 4 hours and 10 hours from the beginning of the test, when the nucleus division occurs.

Figure 10A:
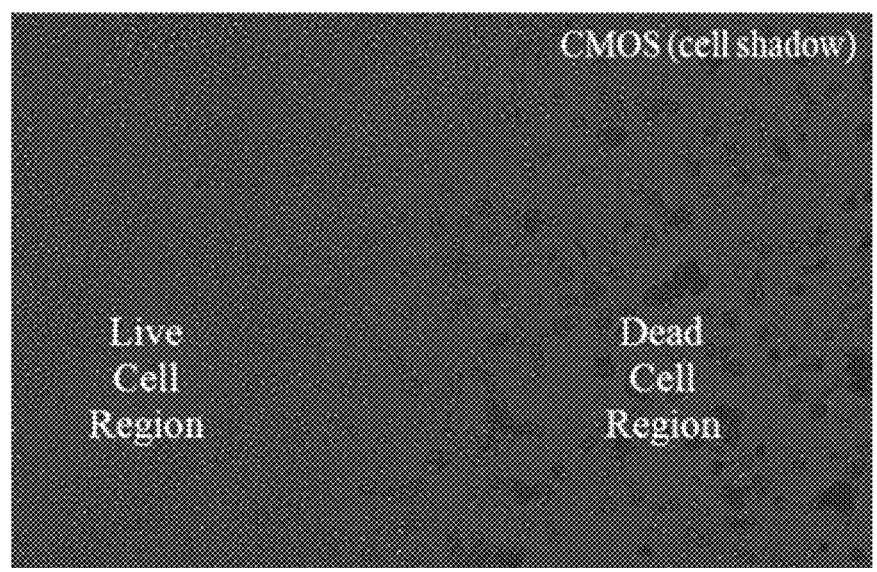
FIG. 10A, FIG. 10B, and FIG. 10C illustrate a shadow image captured by the cell activity measurement apparatus of FIG. 1 in which live cells and dead cells are both present.

FIG. 10A illustrates a shadow image captured by the cell activity measurement apparatus of FIG. 1 in which live cells and dead cells are both present.

For a comparative measurement of cell activity, cells were cultivated in the cell activity measurement apparatus 100 for an extended period, after which heat was applied to some cell colonies to cause them to die. The test was performed such that one sheet of the shadow image captured by the image sensor 140 includes thousands of normal cell colonies (left) and dead cell colonies (right), as in FIG. 10A. As a result, the living and dead cells could be clearly differentiated under a microscope, as shown in FIG. 10B and FIG. 10C.

Figure 10B:
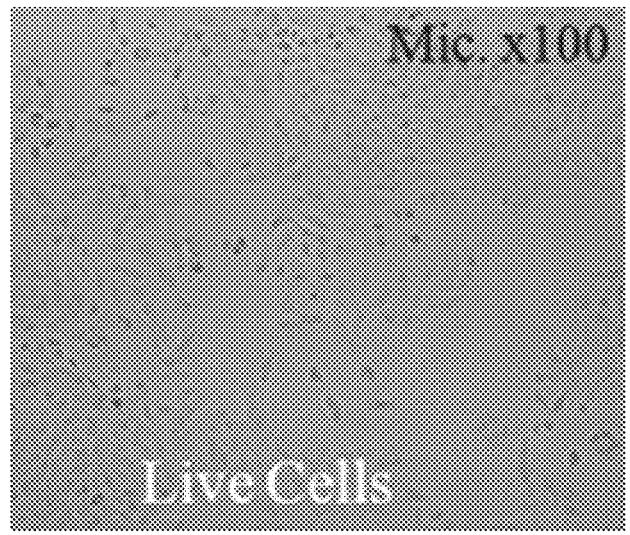
Figure 10C:
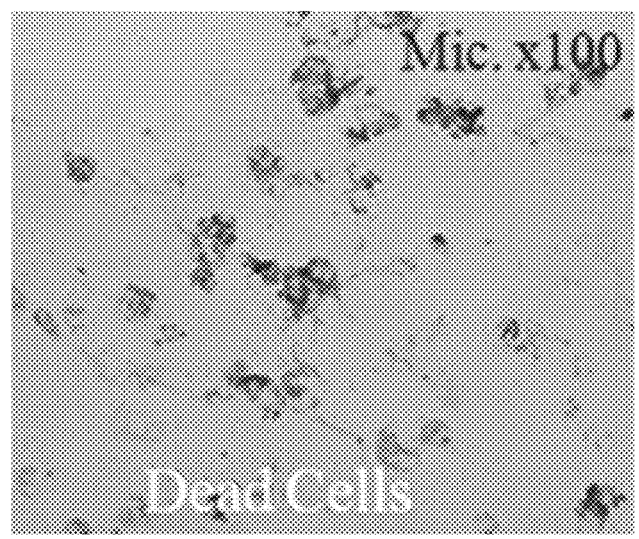

As can be seen from FIGS. 10A to 10C, the cell activity measurement apparatus 100 can observe cell activity to a greater extent compared to the microscope.

Figure 11A:
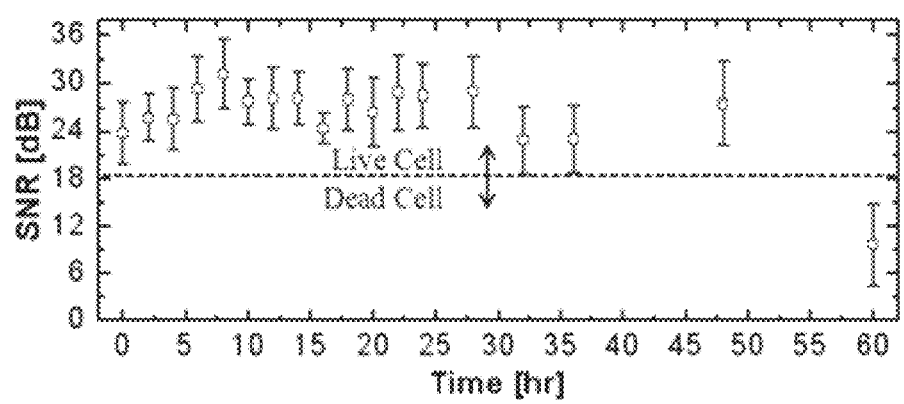
FIG. 11A, FIG. 11B, and FIG. 11C illustrate the shadow image of FIG. 10A via an image processing technique.
Figure 11B:
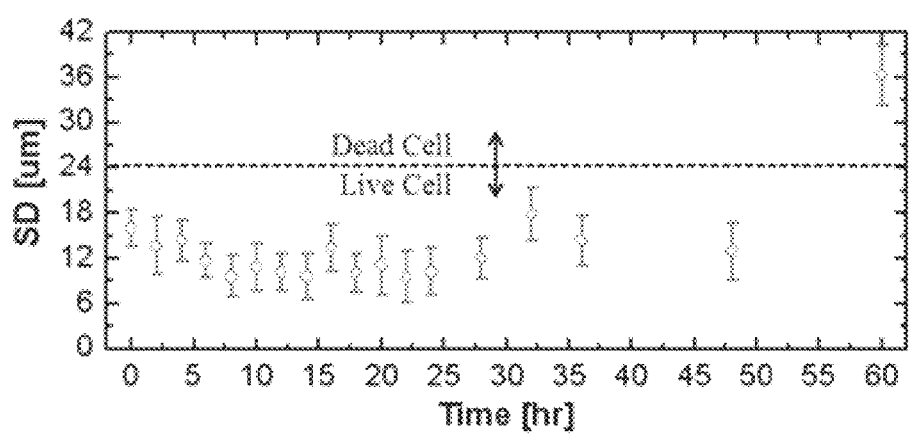
Figure 11C:
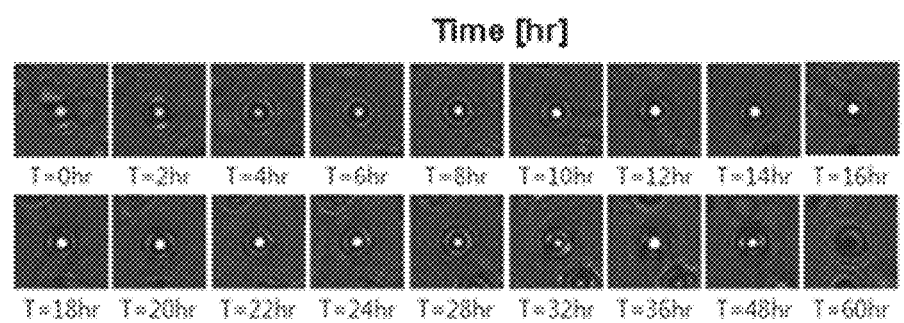

FIGS. 11A to 11C illustrate the shadow image of FIG. 10A via an image processing technique.

To quantify the live and dead cell colonies using the shadow image, FIGS. 11A to 11C employ the SNR and SD values defined above and show changes in these values for the living and dead cell colonies.

As shown in FIG. 11A and FIG. 11B, between cells that are living and cells that are dead, a greater magnitude of change in the SNR and SD can be observed compared to what was observed during the nucleus division of a cell. FIG. 11C shows how the shadow pattern of a particular cell changes during a period of 60 hours.

FIGS. 12A to 12D are diagrams for describing a method of digitizing the number of cells in a cell activity analysis method related to an embodiment of the present invention.

By observing changes in thy: SNR and SD values of a shadow pattern, it is possible to establish quantified criteria for determining whether a cell is living or dead. Also, an embodiment of the present invention can include an operation of choosing certain pixels by using the degrees of similarity, between the pixels of the cell's shadow image and a particular shape. From among the pixels forming the shadow pattern of a cell, those pixels can be chosen and specified of which the circularity corresponds to a particular range. In this way, linearly shaped dust particles, etc., that are differently shaped from the shadow pattern of a cell, which is close to a circle, can be effectively identified and removed. The measurement of the circularity of pixels can be calculated by dividing the smaller of a shadow pattern's lateral length and longitudinal length by the greater. A shadow image that is shaped as a perfect circle would have a circularity value of 1, while a lower circularity can have a value between 0 and 1.

Figure 12A:
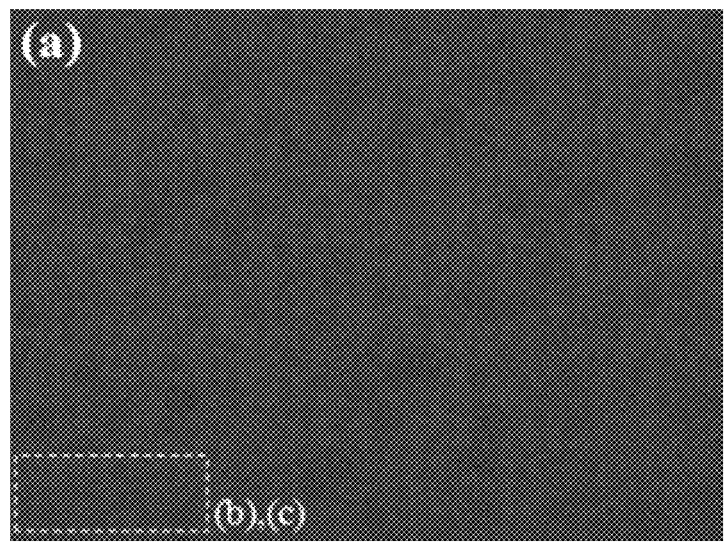
FIG. 12A, FIG. 12B, FIG. 12C, and FIG. 12D are diagrams for describing a method of digitizing the number of cells in a cell activity analysis method related to an embodiment of the present invention.

FIG. 12A shows an example in which a preliminary evaluation is performed regarding whether the cells are living or dead by using SNR values extracted from the cells' shadow image (the area above the dotted line in FIG. 11A represent living cells), and an image processing technique is used to indicate red pixels. In the preliminary evaluation, pixels having a particular SNR value (approximately 18 dB) or higher were chosen and specified in red in the overall shadow image.

Figure 12B:
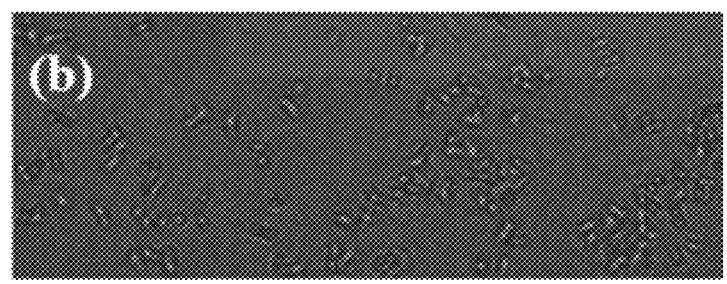
Figure 12C:
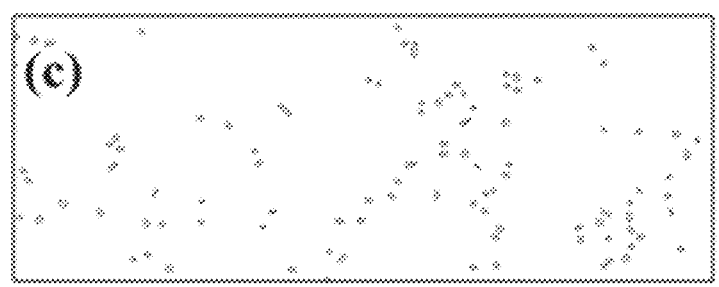

FIG. 12B is an image showing a particular portion of FIG. 12A in a digitally magnified form. When a secondary evaluation is performed regarding whether the cells are living or dead by using SD values (the area below the dotted line in FIG. 11B represent living cells), only the normal cells are shown in a silhouette form, as illustrated in FIG. 12C.

In the secondary evaluation, the pixel clusters of which the SD is smaller than or equal to a particular value (approximately 24 μm) and at the same time the circularity of the pixels has a value between 0.3-1.0 are selectively specified from among the red pixel clusters selected from the preliminary evaluation.

Next, only the shadow images for cells that are thought to be alive after the preliminary and secondary evaluation are counted, for a numerical representation of the cells' activity.

Figure 12D:
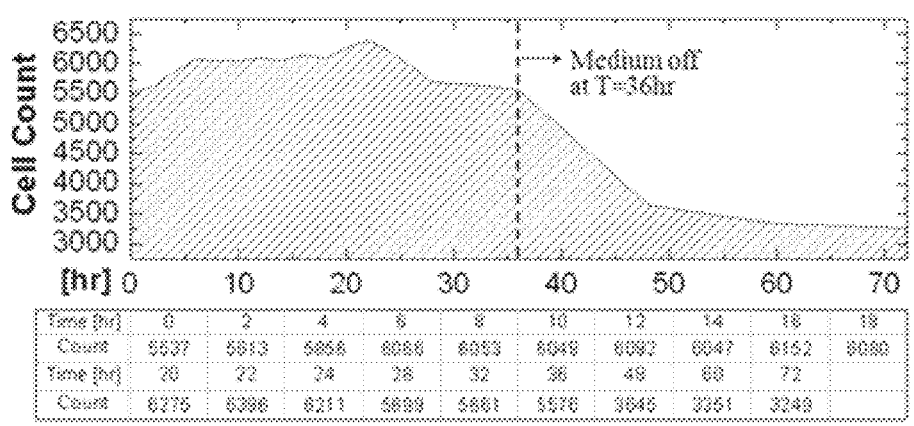

FIG. 12D shows a digitization by an image processing technique of the silhouette images for which the two-step evaluation of cells using SNR and SD were completed. In this way, the activity of the cells can be conclusively quantified. FIG. 12D shows the results of counting the living cells remaining after stopping the supply of culture fluid at T=36 hr, in order to clearly present the quantification process of the cells' activity.

As can also be seen from the test example described above, a cell activity measurement apparatus 100 related to an embodiment of the present invention can observe a large amount of cells continuously without requiring a separate reagent. The cell activity measurement apparatus 100 makes it possible to distinguish a nucleus division in a cell or distinguish live and dead cells, which in the past was observable only by means of an expensive microscope, etc., using a separate dyeing reagent, etc.

In particular, a cell activity measurement apparatus according to an embodiment of the present invention makes it possible to perform cytotoxicity tests, which are essential in developing new drugs, or perform measurements or evaluations of microorganism activity in relation to environments and foods with lost cost and in a speedy manner.

Moreover, work that could only be performed in the past by experienced examiners or technicians who are capable of using various cell activity measurement equipment such as a microscope, etc., can be automated with the development of computer software coupled with a simple image processing technique, with the results of decreased costs and greatly reduced errors in measurement.

The cell activity analysis method described above can be implemented in the form of program instructions that may be performed using various computer means and can be recorded in a computer-readable medium. Such a computer-readable medium can include program instructions, data files, data structures, etc., alone or in combination. The program instructions recorded on the medium can be designed and configured specifically for the present invention or can be a type of medium known to and used by the skilled person in the field of computer software.

Examples of a computer-readable medium may include magnetic media such as hard disks, floppy disks, magnetic tapes, etc., optical media such as CD-ROM's, DVD's, etc., magneto-optical media such as floptical disks, etc., and hardware devices such as ROM, RAM, flash memory, etc.

Examples of a computer-readable medium can also include a transmitting medium such as light, metal lines, waveguides, etc., that transmits signals for specifying program instructions, data structures, etc.

Examples of the program of instructions may include not only machine language codes produced by a compiler but also high-level language codes that can be executed by a computer through the use of an interpreter, etc. The hardware mentioned above can be made to operate as one or more software modules that perform the actions of the embodiments of the invention, and vice versa.

The cell activity measurement apparatus and cell activity analysis method described above are not to be limited in their application to the compositions and methods of the embodiments described above. Rather, some or all of each of the embodiments may be selectively combined to form numerous variations.

What is claimed is:

1. A cell activity measurement apparatus comprising:
a fluidic channel configured to receive a culture fluid and cells injected therein;
an RGB light-emitting diode (LED) positioned over the fluidic channel and configured to emit light in a direction of the fluidic channel;
an image sensor positioned under the fluidic channel and configured to capture a shadow image of the cells; and
an analysis module configured to
calculate a SNR (signal-to-noise ratio) value and SD (shadow diameter) value from the shadow image, and
analyze an activity state of the cells based on the SNR value and the SD value extracted from the shadow image,
wherein
the SNR value is a difference between a maximum intensity value of pixel configuring a shadow of a cell in the shadow image and an average intensity value of background which is free of the pixel configuring the shadow of the cell, and
the SD value is a shadow diameter of the cell in the shadow image, wherein the analysis module includes a processor and a memory storing a software module, and said processor is, by executing the software module, configured to:
receive the shadow image from the image sensor;
extract the SNR and SD values in the shadow image,
calculate the SNR value and SD value from the received shadow image; and
wherein the shadow image is a circular image in which a bright ring and a dark ring appear in an alternating manner
wherein the fluidic channel comprises a flow cell having an inlet and outlet and configured to have the culture fluid and the cell injected therein and discharged therefrom,
a wall positioned under the flow cell, and a cover glass positioned at a lower end of the wall, wherein the wall is made from polydimethylsiloxane (PDMS),
wherein the flow cell covers the wall so that the wall includes a hollow middle portion to provide a space between flow cell and the cover glass
wherein the processor is configured to
select cells having a predetermined SNR value or higher in the received shadow Image,
determine, among the selected cells, a cell having a predetermined SD value or lower is living, and
output time-lapse graphs of the calculated SNR value and SD value in order to display the activity state of the cells for cell activity analysis on a display part.

2. The cell activity measurement apparatus of claim 1, further comprising:
a pinhole coupled to a lower end portion of the RGB LED.

3. The cell activity measurement apparatus of claim 1, further comprising:
a temperature adjustment part arranged to surround the fluidic channel and configured to maintain the culture fluid and cell at a constant temperature in the fluidic channel.

* * * * *